United States Patent
Suzuki et al.

(10) Patent No.: US 8,126,659 B2
(45) Date of Patent: Feb. 28, 2012

(54) COMPUTATIONAL METHOD OF MATERIAL CONSTANT OF COMPOSITE MATERIAL AND VOLUME FRACTION OF MATERIAL COMPONENT IN COMPOSITE MATERIAL, AND RECORDING MEDIUM

(75) Inventors: Nobuo Suzuki, Kanagawa (JP); Kazuyuki Kabe, Kanagawa (JP); Seiichi Nomura, Arlington, TX (US)

(73) Assignee: The Yokohama Rubber Co., Ltd., Tokyo (JP)

( * ) Notice: Subject to any disclaimer, the term of this patent is extended or adjusted under 35 U.S.C. 154(b) by 477 days.

(21) Appl. No.: 12/396,097

(22) Filed: Mar. 2, 2009

(65) Prior Publication Data
US 2010/0223017 A1 Sep. 2, 2010

(51) Int. Cl.
*G01L 1/00* (2006.01)
*G06F 17/00* (2006.01)
*G06F 7/00* (2006.01)
*B32B 15/00* (2006.01)

(52) U.S. Cl. ............... 702/42; 703/2; 708/446; 428/615

(58) Field of Classification Search ............... 702/42
See application file for complete search history.

(56) References Cited

U.S. PATENT DOCUMENTS

| | | | | |
|---|---|---|---|---|
| 5,170,367 A | * | 12/1992 | Mackay et al. | 702/22 |
| 2003/0060987 A1 | * | 3/2003 | Dao et al. | 702/42 |
| 2003/0216894 A1 | * | 11/2003 | Ghaboussi et al. | 703/2 |
| 2006/0095493 A1 | * | 5/2006 | Kumano et al. | 708/490 |
| 2007/0075450 A1 | * | 4/2007 | Belegundu et al. | 264/40.1 |
| 2007/0100565 A1 | * | 5/2007 | Gosse et al. | 702/34 |

FOREIGN PATENT DOCUMENTS

| | | |
|---|---|---|
| JP | 2003-347301 A | 12/2003 |
| JP | 2007-122242 A | 5/2007 |
| JP | 2007-265382 A | 10/2007 |

\* cited by examiner

*Primary Examiner* — Drew A Dunn
*Assistant Examiner* — Rhadames J Alonzo Miller
(74) *Attorney, Agent, or Firm* — Global IP Counselors, LLP

(57) ABSTRACT

In computing the overall material constant of a composite material, a virtual composite material is defined as the one that predetermined material components are dispersed in a form of spherical particles in a matrix phase at known volume fractions, and a nonlinear equation having the overall material constant of the virtual composite material as an unknown is prepared. Next, the overall material constant of the composite material is computed by solving the nonlinear equation. The nonlinear equation is a recursive nonlinear equation which is obtained by defining the material constant in the surrounding areas of the spherical particles as the overall material constant of the composite material to be computed. The volume fraction of a material component dispersed in the composite material is computed using the recursive nonlinear equation.

24 Claims, 8 Drawing Sheets

US 8,126,659 B2

COMPUTATIONAL METHOD OF MATERIAL CONSTANT OF COMPOSITE MATERIAL AND VOLUME FRACTION OF MATERIAL COMPONENT IN COMPOSITE MATERIAL, AND RECORDING MEDIUM

BACKGROUND OF THE INVENTION

1. Field of the Invention

The present invention relates to a method of computing the overall mechanical material constant, as a mechanical characteristic, of a composite material which includes material components having known material constants embedded in a matrix phase having a known material constant. Additionally, the present invention relates to a method of computing the volume fraction of a material component in a composite material in which other material components having known material constants are dispersed in a matrix phase having a known material constant. Furthermore, the present invention relates to a recording medium storing a program for causing a computer to execute the aforementioned methods.

2. Description of the Related Arts

Conventionally, a variety of attempts have been actively employed for accurately estimating the mechanical characteristic of a composite material in which predetermined material components are dispersed in a matrix phase. The estimation intends to efficiently identify a variety of factors using a computer for tailoring the composite material to have a desired characteristic, instead of finding them by an actual experiment. For example, the factors may include identification of the mechanical characteristics of the material components in the composite material and the volume fractions of the material components. As a result, it is possible to design a mixture of components with desired characteristics in an early stage.

Under the circumstance, JP-A-2007-122242 discloses a method for analyzing a macro-structure which consists of multiple minute elements in which a micro-structure that has a three-dimensionally heterogeneous deformation characteristic is repeated periodically in one direction. In the publication, the homogenized elastic modulus is computed by identifying a unit cell (i.e., a periodic unit in the macro-structure) and assuming the unit cell to have a homogeneous material characteristic. Subsequently, the macro-structure is modeled by assuming that it has a homogenized elastic characteristic. Then, a macro-scale analysis is executed for computing the deformation of the macro-structure at a given position in the direction of the periodical arrangement. Furthermore, a local analysis is executed. In the local analysis, the obtained deformation of the macro-structure at a given position in the direction of the periodical arrangement is applied to the minute elements forming the unit cell arranged in the position, and local responses are obtained from the minute elements.

According to the publication, the structural analysis method is capable of reducing a period of time required for the structural computation of the macro-structure which is heterogeneous on its cross-section.

However, the structural analysis method is executed using a finite element model formed with minute elements. Accordingly, the method has a drawback in that a long period of time is necessary for generation of a model and computation and it cannot be thereby a useful means for time-critical initial design and development in the early stage.

On the other hand, a classical analytical model, using a spring and a dash pot, has also been conventionally used for computing the mechanical characteristic of composite materials. The model spends a short period of time for computation, and is efficient in this regard. However, the micro-state of a composite material cannot be taken into account in the model. Therefore, the model also has a drawback in that a computational result does not include much information and thereby the computational result is not accurate.

SUMMARY OF THE INVENTION

In order to overcome the drawback, it is an object of the present invention to provide a method of computing the material constant of a composite material and a method of computing the volume fraction of a material component in the composite material, for more efficient computation in a shorter period of time than the conventional computational method using a finite element model, and for more accurately achieving computation and including much information in a computation result to be obtained than a classical analysis model with a spring and a dash pot. Furthermore, it is an object of the present invention to provide a recording medium storing a program for causing a computer to execute the methods.

It is possible to achieve the objects by a method of computing the overall mechanical material constant of a composite material which consists of a first material component in a matrix phase, each of the material constants of the first material component and the matrix phase being known. The method includes the following steps of:

(A) preparing a nonlinear equation having the material constant of a virtual composite material as an unknown by defining the virtual composite material in which the first material component is dispersed in a form of spherical particles in the matrix phase at a known volume fraction; and (B) computing the material constant of the virtual composite material as the overall material constant of the composite material by solving the prepared nonlinear equation, (C) In this case, the nonlinear equation is a recursive nonlinear equation which is obtained by defining a material constant in the surrounding areas of the spherical particles in the virtual composite material as the material constant of the virtual composite material to be computed.

Additionally, it is possible to achieve the aforementioned objects by a method of computing the overall mechanical material constant of a composite material which includes a first material component and a second material component in a matrix phase, each of the material constants of the first material component, the second material component and the matrix phase being known. The method includes the steps of:

(D) preparing a first nonlinear equation having the overall material constant of the first virtual composite material as an unknown by defining the first virtual composite material in which the first material component is dispersed in a form of spherical particles in the matrix phase at a known volume fraction;

(E) computing the overall material constant of the first virtual composite material by solving the prepared first nonlinear equation;

(F) preparing a second nonlinear equation having the material constant of a second virtual composite material as an unknown by defining the second virtual composite material in which the second material component is dispersed in a form of spherical particles in a virtual matrix phase having the computed material constant of the first virtual composite material at a known volume fraction; and (G) computing the material constant of the second virtual composite material as the overall material constant of the composite material by solving the prepared second nonlinear equation, and (H) In this case, the first nonlinear equation is a recursive nonlinear equation which is obtained by defining the material constant in the surrounding areas of the spherical particles as the overall material constant of the first virtual composite material to be computed, and the second nonlinear equation is also a recursive nonlinear equation which is obtained by defining the material constant in the surrounding areas of the spherical particles as the material constant of the second virtual composite material to be computed.

Furthermore, it is possible to achieve the aforementioned objects by a method of computing the volume fraction of a first material component in the composite material which includes the first material component in the matrix phase, each of the material constants of the first material component and the matrix phase being known. The method includes the steps of:

(I) determining the overall material constant of the composite material from an experimental result;

(J) preparing a nonlinear equation having the volume fraction of the first material component in the virtual composite material as an unknown by defining the virtual composite material in which the first material component is dispersed in a form of spherical particles in the matrix phase; and (K) computing the volume fraction of the first material by solving the prepared nonlinear equation, and (L) In this case, the nonlinear equation is a recursive nonlinear equation which is obtained by defining the material constant in the surrounding areas of the spherical particles in the virtual composite material as the determined material constant of the composite material.

Moreover, it is possible to achieve the aforementioned objects by a method of computing the volume fraction of the second material component in the composite material which includes the first material component and the second material component in the matrix phase, each of the material constants of the first material component, the second material component and the matrix phase being known. The method includes the steps of:

(M) determining the overall material constant of the composite material from an experimental result;

(N) preparing a third nonlinear equation having the volume fraction of the second material as an unknown by defining the first virtual composite material in which the first material component is dispersed in a form of spherical particles in the matrix phase at a known volume fraction and by further defining the second virtual composite material in which the second material component is dispersed in a form of spherical particles in a virtual matrix phase having the overall material constant of the first virtual composite material at a unknown volume fraction; and (O) computing the volume fraction of the second material component by solving the prepared third nonlinear equation, and (P) In this case, the third nonlinear equation is a recursive nonlinear equation which is obtained by defining the material constant in the surrounding areas of the spherical particles in the first virtual composite material as the overall material constant of the first virtual composite material and by defining the material constant in the surrounding areas of the spherical particles in the second virtual composite material as the determined material constant of the composite material.

Furthermore, it is possible to achieve the aforementioned objects by a recording medium storing a computer-executable program, using the aforementioned computational methods, for computing the overall material constant of the composite material which includes the first material component in the matrix phase where each of the material constants of the first material component and the matrix phase being known.

Also, it is possible to achieve the aforementioned objects by a recording medium storing a computer-executable program for computing, using the aforementioned computational methods, for computing the overall mechanical material constant of composite material which includes a first material component and a second material component in a matrix phase, each of the material constants of the first material component, the second material component and the matrix phase being known.

Similarly, it is possible to achieve the aforementioned objects by a recording medium storing a computer-executable program for computing the volume fraction of the first material component in the composite material which includes the first material component in the matrix phase, each of the material constants of the first material component and the matrix phase being known.

Furthermore, it is possible to achieve the aforementioned objects by a recording medium storing a computer-executable program for computing the volume fraction of the second material component in the composite material which includes the first material component and the second material component in the matrix phase, each of the material constants of the first material component, the second material component and the matrix phase being known.

The recursive nonlinear equation, common to the aforementioned computational methods, is based on Equation (5) to be described. Specifically, the proportional constant A in Equation (5), used for the recursive nonlinear equation, is computed by obtaining the strain field of the virtual composite material using the Navier equation. In this case, the material constant in the surrounding areas of the spherical particles in the virtual composite material is defined as the overall material constant of the virtual composite material. In other words, the self-consistent approximation method is herein used.

According to the aforementioned computational methods, the virtual composite material, where predetermined materials are dispersed in a form of spherical particles in the matrix phase, is defined as the composite material. Furthermore, the nonlinear equation to be used therein is an analytic recursive nonlinear equation which is obtained by defining the material constant in the surrounding areas of the spherical particles in the virtual composite material instead of the material constant of the matrix phase as the material constant of the virtual composite material to be computed. Therefore, the aforementioned method is capable of efficiently computing the overall material constant of the composite material and the volume fraction of a material component in the composite material in a short period of time.

DETAILED DESCRIPTION OF THE EMBODIMENTS

Following is a detailed explanation of the method of computing the material constant of a composite material according to the present invention and the method of computing the volume fraction of a material component in a composite material according to the present invention. The explanation is based on an embodiment illustrated in the attached drawings.

Figure 1:
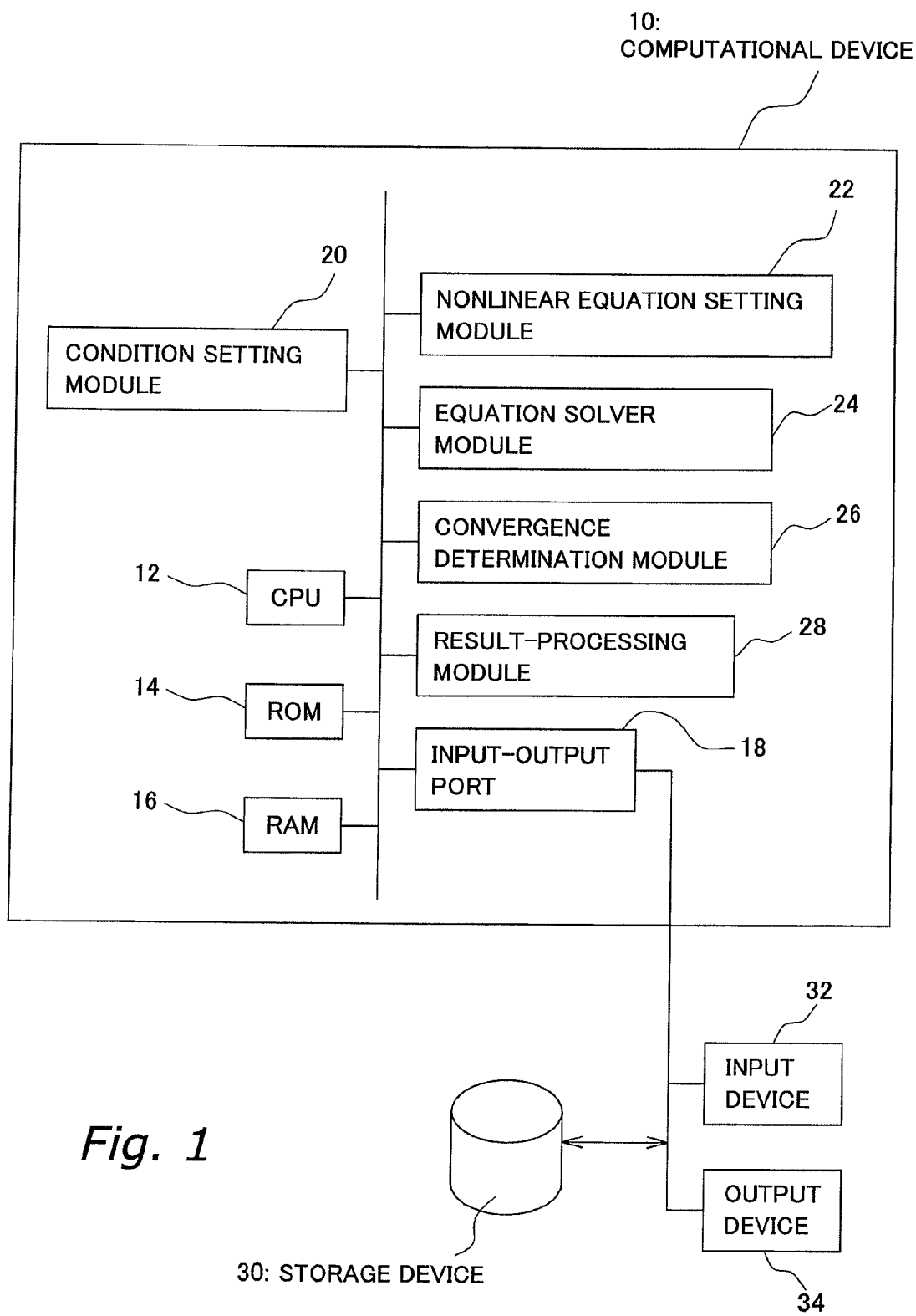
FIG. 1 is a schematic diagram for illustrating an example of a computational device for executing both of the methods of computing the material constant of a composite material according to the present invention and computing the volume fraction of a material component in the composite material according to the present invention.

FIG. 1 illustrates a configuration of a computational device 10 for executing the method of computing the material constant of a composite material and the method of computing the volume fraction of a material component in a composite material.

The computational device 10 is composed of a computer including a CPU 12, ROM 14, RAM 16 and an input-output port 18. Additionally, the computational device 10 is connected to a storage device 30, an input device 32 (e.g., a mouse and a keyboard), an output device 34 (e.g., a printer and a monitor) and the like through the input-output port 18.

The computational device 10 configures a condition setting module 20, a nonlinear equation setting module 22, an equation solver module 24, a convergence determination module 26 and a result-processing module 28 invoked when a program stored in the storage device 30 starts up. In other words, the modules are invoked when the software is started. For example, some the modules of the computational device 10 use a computer algebra system.

The computational device 10 selectively executes either one of:

(1) the first processing for computing the overall mechanical material constant of the composite material which includes at least one kind of a material component having a known mechanical material constant in a matrix phase having a known mechanical material constant; and (2) the second processing for computing the volume fraction of a material component in a composite material which includes a single or multiple kinds of material components having a known material constant(s) in a matrix phase having a known material constant. Note the term "mechanical material constant" is hereinafter simply referred to as "material constant."

The condition setting module 20 determines which of the first processing or the second processing will be executed. Simultaneously, the module 20 prepares information necessary for the first processing or the second processing and sets a variety of values based on the information.

In the first processing, the module 20 sets values of the material constant of the matrix phase, the material constant(s) of a single or multiple kinds of material components and the volume fraction(s) of the single or multiple kinds of material components. For example, the material constant herein includes a pair of the Lamé constants $\lambda$, $\mu$, or a pair of the bulk modulus K and either one of the Lamé constants $\lambda$ or $\mu$. A pair of the Lamé constants $\lambda$, $\mu$ will be hereinafter mainly used. However, it is also acceptable to use a pair of the bulk modulus K and either one of the Lamé constants $\lambda$ or $\mu$.

In the second processing, on the other hand, the module 20 sets the value of the overall material constant of the composite material obtained by an experiment, the value(s) of a material constant(s) of a single or multiple kinds of material components and the value(s) of a volume fraction(s) of the single or multiple kinds of material components.

The values are set by an instruction inputted by an operator through the input device 32. Alternatively, the values are set by calling up preliminarily stored information from the storage device 30.

The nonlinear equation setting module 22 prepares a nonlinear equation, depending on the first processing or the second processing, with the value of the material constant and the value of the volume fraction which have been set by the module 20. In both of the first processing and the second processing, when the composite material is assumed to includes one kind of material component in a matrix phase, the module 22 calls up a recursive nonlinear equation for computing the overall material constant of the composite material (i.e., Equation (5) to be described), and gives appropriate values to the coefficients of the equation based on the material constants and the volume fraction. Consequently, an equation, composed of unknowns to be computed, is herein prepared.

In the first processing, the equation solver module 24 computes the overall material constant of the composite material based on its initial approximation value using the prepared recursive nonlinear equation employing the Newton-Raphson method. In other words, the module 24 firstly sets an initial value (where n=1) of the overall material constant of the composite material. Then, the module 24 iteratively computes an approximate value of the overall material constant of the composite material (where n=2), that is, a more closely convergent value, based on the recurrence formula using the initial value. The more closely convergent value is transmitted to the convergence determination module 26 to be described later. When the module 26 determines that the value is not convergent, the module 24 repeats the computation of the overall material constant of the composite material (where n=3), that is, a further closely convergent value, based on the aforementioned recurrence formula using the previously computed value of the overall material constant. Thus, the module 24 repeatedly executes processing for recursively computing the value of the overall material constant of the composite material until the module 26 determines that convergence of the value is reached.

In the second processing, on the other hand, the equation solver module 24 defines the following function f(x) (note "x" is the volume fraction of a predetermined material component to be computed). Then, the module 24 computes a product $f(x_1) \cdot f(x_2)$ by multiplying $f(x_1)$ (where $x=x_1$ (maximum)) and $f(x_2)$ (where $x=x_2$ (minimum)). The module 24 transmits the product to the convergence determination module 26.

The function $f(x)$=(the overall material constant of the composite material obtained by an experiment)−(the overall material constant of the composite material having the volume fraction x to be computed from the recursive nonlinear equation (5)).

The product $f(x_1) \cdot f(x_2)$ is repeatedly computed until convergence is reached while the maximum value ($x=x_1$) and the minimum value ($x=x_2$) are changed.

The convergence determination module 26 determines if the overall material constant of the composite material computed by the equation solver module 24 is convergent.

In the first processing, when the absolute value of the difference between the value of the overall material constant of the composite material computed at the number of repetition (n+1) and the value of the overall material constant of the composite material computed at the number of repetition (n) is less than a preliminarily-set threshold, the convergence determination module 26 determines that the value of the overall material constant of the composite material at the number of repetition (n+1) is convergent. Otherwise, the module 26 determines that the overall material constant of the composite material at the number of repetition (n+1) is not convergent. Consequently, the equation solver module 24 is instructed to execute computation with the obtained value at the number of repetition (n+1). As described above, the recursive nonlinear equation is an equation with explicit numeric values given to the coefficients. Accordingly, the derivative of such a function is also easily computed. Therefore, the module 26 is capable of computing the converged value using the Newton-Raphson method.

In the second processing, on the other hand, the sign of $f(x_1) \cdot f(x_2)$ is checked. Then, as described below, the maximum value and the minimum value of x are set again using the bisection method.

The result processing module 28 computes the overall Young modulus and overall shear stiffness of the composite material or obtains the volume fraction of a material component based on the value determined as a converged solution by the module 26.

The output device 34 prints out a variety of information obtained by the module 28. Alternatively, the output device 34 displays the variety of information on a screen.

The storage device 30 preliminarily stores a database having recorded and held preliminarily-set material constants of the composite material and preliminarily-set material constant(s) of a single or multiple kinds of material components included in the composite material.

When a composite material is assumed to include two different kinds of material components β and γ in a matrix phase α, the equation solver module 24 firstly defines a homogeneous first virtual composite material where the material component β is dispersed in the matrix phase α, and then computes the overall material constant of the first virtual composite material. Subsequently, the module 24 computes the overall material constant of a second virtual composite material that the material component γ is dispersed in the virtual composite material. In this case, the former processing for computing the overall material constant of the first virtual composite material and the latter processing for computing the overall material constant of the second virtual composite material are sequentially executed. Therefore, the condition setting module 20, the nonlinear equation setting module 22, the equation solver module 24, the convergence determination module 26 and the result processing module 28 are used for both of the former processing and the latter processing.

The aforementioned processings are achieved by analytically computing the overall material constant of the composite material using the following recursive nonlinear equation. The following is a detailed explanation of the recursive nonlinear equation.

Figure 2A:
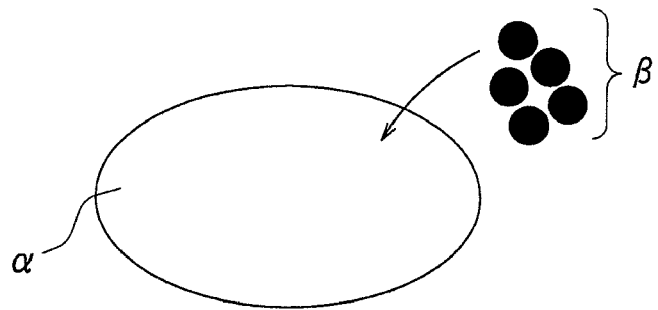
FIGS. 2A, 2B and 2C are diagrams for illustrating the stress and strain in a composite material.
Figure 2B:
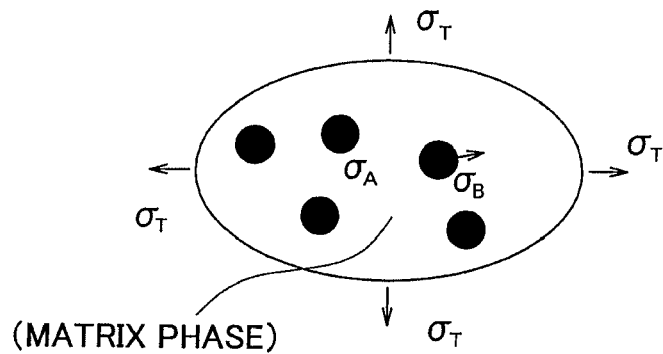
Figure 2C:
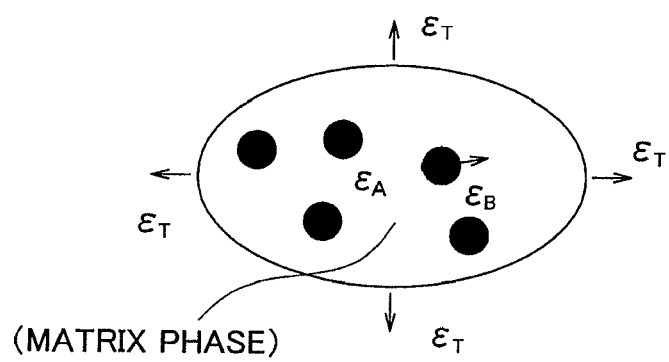

FIGS. 2A to 2C are diagrams for illustrating the composite material.

"Stress," "strain" and "material constant," hereinafter explained, are a second rank tensor, a second rank tensor and a fourth rank tensor, respectively. However, they will be denoted as a scalar form for easy understanding.

As illustrated in FIG. 2A, the composite material is composed of a matrix phase α and a material component β which is included in the matrix phase α. The volume fractions of the matrix phase α and the material component β are herein defined as $v_A$ and $v_B$, respectively.

As illustrated in FIG. 2B, in the composite material, the average stress $\sigma_T$ of the composite material is computed by volume-averaging the stress $\sigma_B$ in the material component β and the stress $\sigma_A$ in the matrix phase α. As illustrated in FIG. 2C, on the other hand, the average strain $\epsilon_T$ of the composite material is computed by volume-averaging the strain $\epsilon_B$ in the material component β and the strain $\epsilon_A$ in the matrix phase α. The average stress $\sigma_T$ is expressed by Equation (1) whereas the average strain $\epsilon_T$ is expressed by Equation (2). The average stress $\sigma_T$ means the volume-weighted average stress whereas the average strain $\epsilon_T$ means the volume-weighted average strain.

Equation 1:

$$\sigma_T = v_A \sigma_A + v_B \sigma_B \quad (1)$$

Equation 2:

$$\epsilon_T = v_A \epsilon_A + v_B \epsilon_B \quad (2)$$

Figure 3A:
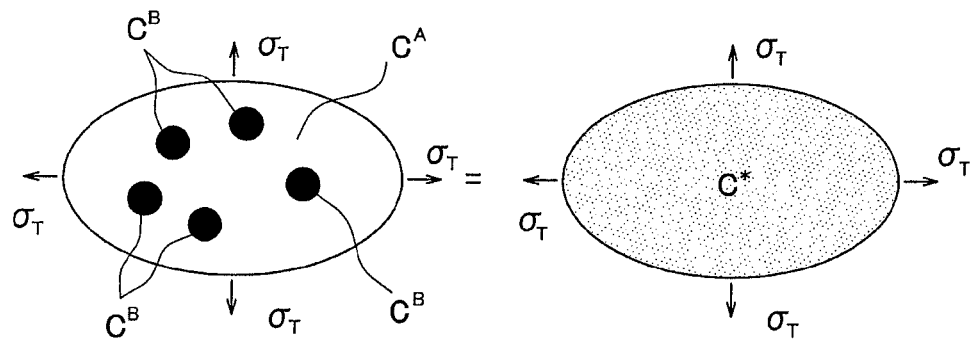
FIGS. 3A and 3B are diagrams for illustrating a virtual composite material to be used for both of the methods of computing the material constant of the composite material according to the present invention and computing the volume fraction of a material component in the composite material according to the present invention.
Figure 3B:
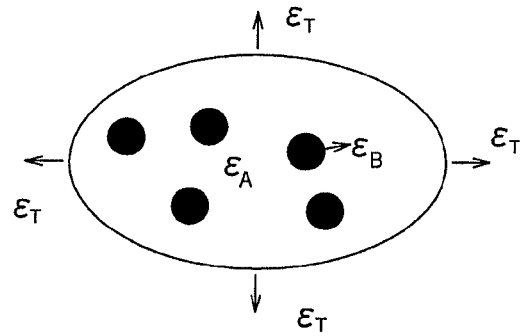

As illustrated in FIG. 3A, on the other hand, the overall material constant C* for defining the relation between the average stress $\sigma_T$ and the average strain $\epsilon_T$ in the composite material is represented by Equation (3). In this case, a homogeneous virtual composite material is assumed to have the material constant C*.

Equation 3:

$$\sigma_T = C^* \epsilon_T \quad (3)$$

When the strain is herein focused, the relation between the strain $\epsilon_B$ in the material component β and the strain $\epsilon_T$ in the composite material is represented using Equation (4).

Equation 4:

$$\epsilon_B = A \epsilon_T \quad (4)$$

In Equation (4), the average strain $\epsilon_B$ in the material β is represented as a function of $\epsilon_T$. Equation (4) states that $\epsilon_B$ is associated with $\epsilon_T$ by a proportional constant A. As described below, the proportional constant A is computed by assuming that the material component β is in a form of spherical particles and each of the surrounding areas of the spherical particles has the material constant of a homogeneous virtual composite material. In other words, it is possible to represent the proportional constant A with the material constant of the material component β and the overall material constant C* of the homogeneous virtual composite material. When the material constant of the material component β is denoted as $C^B$, the proportional constant A is represented using an expression "$A=A(C^B, C^*)$." A method of computing the formula "$A=A(C^B, C^*)$" will be hereinafter explained. The expression "$A(C^B, C^*)$" is a nonlinear complex expression of $C^B$ and C*.

In this case, $C^B$ represents the Lamé constants $\lambda^B$, $\mu^B$ of the material component β whereas $C^*$ represents the Lamé constants $\lambda^*$, $\mu^*$ of the virtual composite material. Equation (5) is derived by organizing Equations (1) to (4) using the proportional constant "$A(C^B,C^*)$.".

Equation (5):

$$C^* = C^A + v_B \cdot (C^B - C^A) \cdot A(C^B, C^*) \quad (5)$$

Equation (5) is a formula for computing the material constant $C^*$ of the left-hand side of the equation. The expression "$A(C^B,C^*)$" of the right-hand side of the equation is a nonlinear expression having $C^*$ as unknowns. Accordingly, Equation (5) is a recursive nonlinear equation having the material constant $C^*$ as an unknown.

Figure 4:
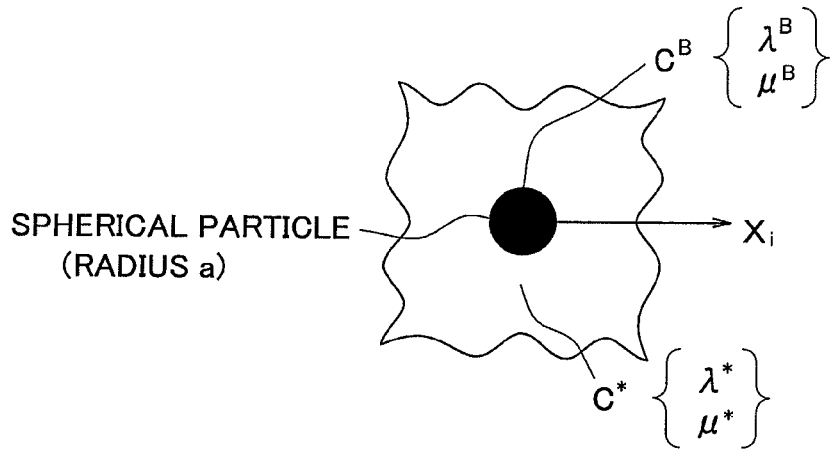
FIG. 4 is a diagram for illustrating the structure of a virtual composite material to be used for the method of computing the material constant of the composite material according to the present invention.

As illustrated in FIG. 4, the proportional constant "$A(C^B, C^*)$" is obtained by assuming a model that the material component β is dispersed in a form of spherical particles in a homogeneous virtual composite material having the material constant $C^*$ and by defining the material constant of the surrounding areas of the spherical particles as the material constant $C^*$ of the virtual composite material to be computed.

In other words, the proportional constant "$A(C^B,C^*)$" is obtained by solving the Navier equation under the condition that body force does not exist but strain $\epsilon^\infty_{ij}$ ("i" and "j" are index numbers of 1-3) is applied at infinity. As illustrated in Equation (6), the strain $\epsilon^\infty_{ij}$, applied at infinity, is decomposed into the hydrostatic pressure term (i.e., a bulk elastic term) and the shear term. Accordingly, the proportional constant "$A(C^B,C^*)$" is computed by decomposing it into the hydrostatic pressure term and the shear term.

Equation (6):

$$\varepsilon^\infty_{ij} = \underbrace{\frac{1}{3}\hat{\varepsilon}^\infty \delta_{ij}}_{\text{1st term}} + \underbrace{\hat{\varepsilon}^\infty_{ij}}_{\text{2nd term}} \quad (6)$$

($\delta_{ij}$: Kronecker delta)

The following is an explanation of the method of computing the hydrostatic pressure term and the shear term in the proportional constant $A(C^B,C^*)$.

(Computation of $A(C^B,C^*)$ Based on Hydrostatic Pressure Term)

The displacement $u_i$ ("i" is an index number of 1-3), satisfying the Navier equation corresponding to the hydrostatic pressure term in Equation (6), is represented using Equation (7). The displacement $u_i$ is uniquely expressed because of the requirement for matching the rank of the displacement tensor $u_i$ with the rank of the tensor in the right-hand side of Equation (7).

Here, it is possible to compute the displacement $u_i$ inside the spherical particle and displacement $u_i$ outside the spherical particle by giving a condition that the displacement $u_i$ at the origin in the spherical particle has a finite value, a condition that the strain is approaching the first term in Equation (6) at infinity, and a condition of continuity of the displacement $u_i$ and the surface traction on the interface of the spherical particle. Specifically, the displacement $u_i$ inside the spherical particle is represented using Equation (8) whereas the displacement $u_i$ outside the spherical particle is represented using Equation (9).

Equation (7):

$$u_i = \left(A + \frac{B}{r^3}\right) x_i \hat{\varepsilon}^\infty \quad (7)$$

($i$ = 1, 2, 3: natural number)

$\begin{cases} r\text{: distance from center of spherical particle,} \\ x_i\text{: three-dimensional coordinate position} \\ A, B\text{: constant} \end{cases}$ Equation (8):

$$u_i = \frac{\lambda^* + 2\mu^*}{3\lambda^B + 2\mu^B + 4\mu^*} x_i \hat{\varepsilon}^\infty \quad (8)$$

Equation (9):

$$u_i = \left(\frac{1}{3} - \frac{1}{r^3} \cdot \frac{3\lambda^B a^3 - 3\lambda^* a^3 + 2\mu^B a^3 - 2\mu^* a^3}{3(3\lambda^B + 2\mu^B + 4\mu^*)}\right) x_i \hat{\varepsilon}^\infty \quad (9)$$

($a$ is radius of spherical particle)

In short, inside the spherical particle, the displacement $u_i$ is proportional to the position $x_i$ (i=1, 2 or 3) where the origin is at the center of the spherical particle. Furthermore, outside the spherical particle, the displacement $u_i$ is proportional to the position $x_i$ (i=1, 2 or 3) where the origin is at the center of the particle, and its proportionality factor has a constant term and a term inversely proportional to the third power of the distance from the center of the spherical particle. Based on this, it is possible to compute the hydrostatic pressure term of the proportional constant "$A(C^B,C^*)$."

Based on Equations (8) and (9), it is possible to represent the stress $\sigma_{ij}$ inside the spherical particle using Equation (10) and the strain $\epsilon_{ij}$ inside the spherical particle using Equation (11). Equation (11) corresponds to the hydrostatic pressure term of Equation (4). Therefore, the hydrostatic pressure term of "$A(C^B,C^*)$" is expressed using Equation (12).

Equation (10):

$$\sigma_{ij} = \frac{(3\lambda^B + 2\mu^B)(\lambda^* + 2\mu^*)}{(3\lambda^* + 2\mu^*)(3\lambda^B + 2\mu^B + 4\mu^*)} \hat{\sigma}^\infty \delta_{ij} \quad (10)$$

Equation (11):

$$\varepsilon_{ij} = \frac{\lambda^* + 2\mu^*}{3\lambda^B + 2\mu^B + 4\mu^*} \hat{\varepsilon}^\infty \delta_{ij} \quad (11)$$

Equation (12):

$$\text{Hydrostatic Pressure Element of } A(C^B, C^*) = \frac{\lambda^* + 2\mu^*}{3\lambda^B + 2\mu^B + 4\mu^*} \quad (12)$$

(Computation of $A(C^B,C^*)$ Based on the Shear Term)

In both outside and inside the spherical particle, the displacement $u_i$ ("i" is an index number of 1, 2 or 3), satisfying the Navier equation corresponding to the shear term in Equation (6), is expressed by terms proportional to the zeroth-power, second-power, inverse third-power and fifth-power of the distance from the center of the spherical particle. This comes from the requirement that the displacement $u_i$ is proportional to "$\{f(r)\cdot(x_ix_j/r^2) + g(r)\cdot\delta_{ij}\}\cdot x_k \epsilon^\infty_{jk}$" (each of "i," "j" and "k" is an index number of 1-3). The equation is uniquely determined because of the requirement for matching the ranks of tensors in the Navier equation. In this case, "$x_j$" and "$x_k$" represent the coordinate components in the three-dimensional coordinate. The coordinate components "$x_j$" and "$x_k$" are different from the coordinate component "$x_i$." Furthermore, the functions f(r) and g(r) are functions of the distance "r" from the center of the spherical particle only. The order l of "r" is herein computed using the order analysis by assuming that f(r) and g(r), satisfying the Navier equation, have the following relations, respectively: $f(r) \propto r^l$ and $g(r) \propto r^l$ ("l" is an integer). As a result, the orders l of "r" are calculated to be 0, 2, −3 and 5. Accordingly, the displacement $u_i$, satisfying the Navier equation, is expressed by a combination of terms proportional to the zeroth-power, second-power, inverse third-power and fifth-power of the distance from the center of the spherical particle both outside and inside the spherical particle. For example, for the order l=2, the equation is expressed by Equation (13). Obviously, the material constants of the spherical particle must be used for $\lambda$ and $\mu$ in Equation (13). For outside the spherical particle, on the other hand, the material constants outside the spherical particle must be used for $\lambda$ and $\mu$ in Equation (13).

Equation (13):

$$u_i = \left( r^2 x_i x_j - \frac{7\mu + 5\lambda}{7\mu + 2\lambda} r^2 \delta_{ij} \right) x_k \hat{\varepsilon}_{jk}^{\infty} \quad (13)$$

In short, it is possible to represent the displacement $u_i$ as a combination of terms proportional to the zeroth-power, second-power, inverse third-power and fifth-power of the distance from the center of the spherical particle both inside and outside the spherical particle. Hence, it is possible to compute the shear term of the proportional constant "$A(C^B,C^*)$" for deriving a recursive nonlinear equation.

Specifically, the stress inside the spherical particle, illustrated in Equation (14), is obtained by giving a condition of continuity of the displacement $u_i$ on the surface of the spherical particle and a condition of continuity of the surface traction on the surface of the spherical particle. Based on Equation (14), the shear term in the proportional constant $A(C^B, C^*)$ is expressed as illustrated in Equation (15).

Equation (14)

$$\sigma_{ij} = \frac{15\mu^B \cdot \{2 \cdot (\mu^*)^2 + \lambda^* \mu^*\} \cdot \hat{\sigma}_{ij}^{\infty}}{\mu^* \{14(\mu^*)^2 + 9\lambda^* \mu^* + 16\mu^B \mu^* + 6\lambda^* \mu^B\}} \quad (14)$$

Equation (15)

$$\text{Shear element of } A(C^B, C^*) = \frac{15\{2(\mu^*)^2 + \lambda^* \mu^*\}}{14(\mu^*) + 9\lambda^* \mu^* + 16\mu^B \mu^* + 6\lambda^* \mu^B} \quad (15)$$

Based on the above explanation, the proportional constant $A(C^B,C^*)$ is determined by Equations (12) and (15). Then, the proportional constant $A(C^B,C^*)$ is substituted into Equation (5) for computing the material constant $C^*$. Accordingly, a recursive nonlinear equation is derived. The recursive nonlinear equation is obtained by first assuming a homogeneous virtual composite material in which the material component β is dispersed in a form of spherical particles in the matrix phase α and next by determining the overall material constant of a composite material where spherical particles are dispersed in the matrix phase whose material constant is of the virtual composite material.

As hereinafter described, a result of the overall material constant of the composite material computed by the computational method of the present invention using the virtual composite material is in good agreement with a result computed by the conventional method using a finite element model which requires a long period of computational time. As a conclusion, the computation result of the present method is highly accurate.

Figure 5A:
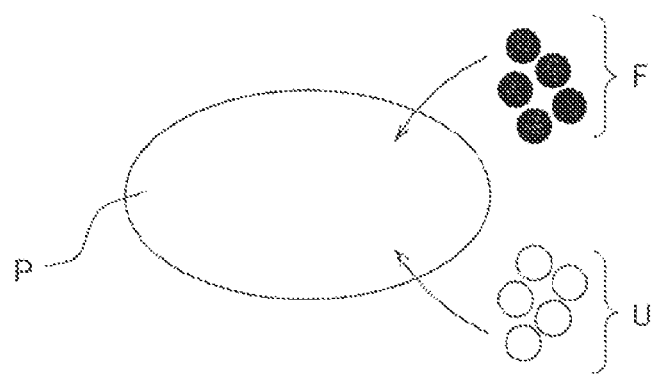
FIGS. 5A, 5B and 5C are diagrams for illustrating an example in which the method of computing the material constant of a composite material according to the present invention is applied to a composite material which includes two different kinds of material components in a matrix phase.
Figure 5B:
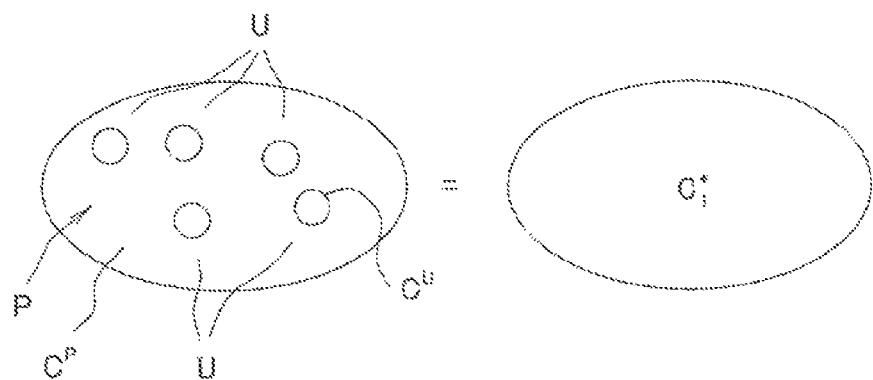
Figure 5C:
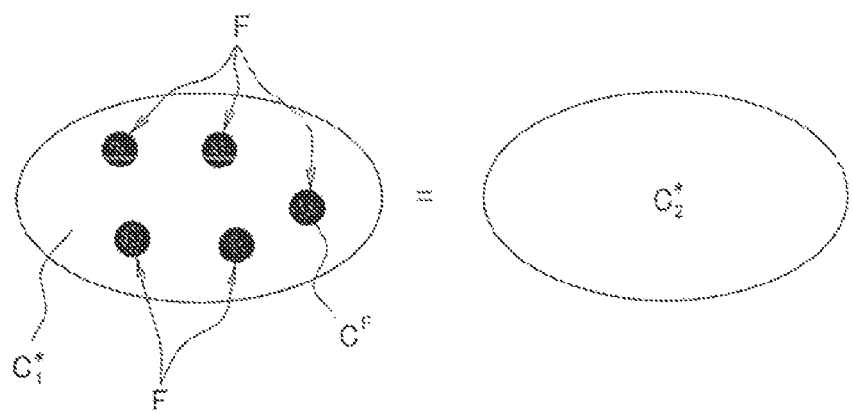

The following is an explanation of the method of computing the overall material constant $C^*$ of the composite material using the recursive nonlinear equation. As illustrated in FIG. 5A, a composite material is composed of epoxy resin P (hereinafter simple referred to as "Epoxy P") used as the matrix phase, and Filler F and Urethane U in Epoxy P as material components. The following is a general explanation of the method. As illustrated in FIG. 5B, as the first step, a first virtual composite material is defined as the one where Urethane U is uniformly dispersed in Epoxy P. In other words, Urethane U is completely resolved and mixed with Epoxy P. The overall material constant of the first virtual composite material is denoted as $C^*_1$. The material constant $C^*_1$ is computed using Equation (5). Next, as illustrated in FIG. 5C, a second virtual composite material is defined as the one where Filler F having the material constant $C^F$ is dispersed in a homogeneous phase having the material constant $C^*_1$ of the first virtual composite material. The overall material constant of the second virtual composite material is denoted as $C^*_2$. The material constant $C^*_2$ is computed as the overall material constant $C^*$ of the composite material using Equation (5).

Figure 6:
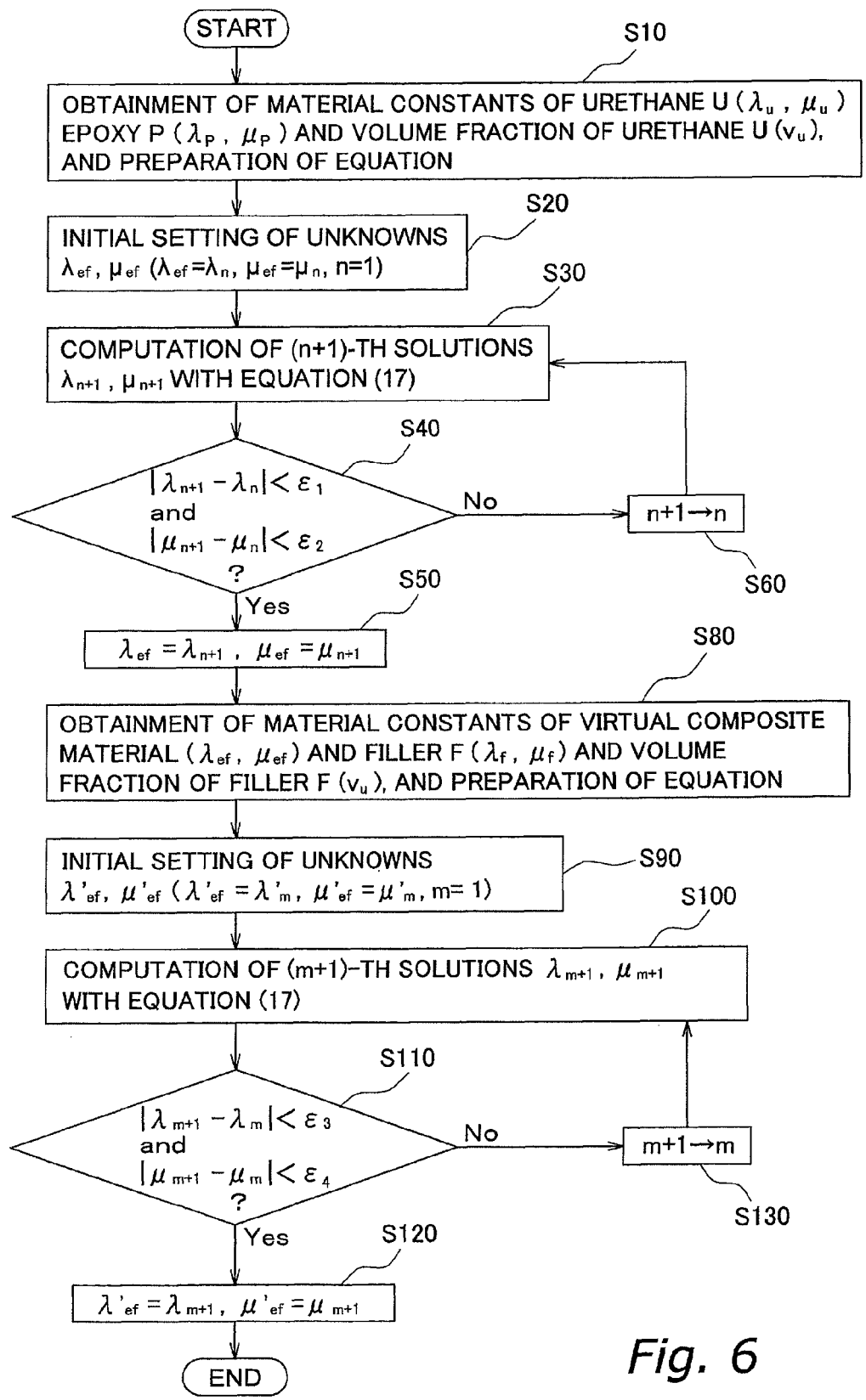
FIG. 6 is a flowchart for illustrating an example of the method of computing the material constant of a composite material according to the present invention.

FIG. 6 is a flowchart for illustrating a series of steps of computing the overall material constant $C^*$.

First, the condition setting module 20 sets the first processing for computing the overall material constant $C^*$ of the composite material. The setting is executed by an instruction inputted by an operator through the input device 32. In this case, the material constant $C^*$ is represented in terms of the Lamé constants $\lambda_{ef}, \mu_{ef}$ (i.e., unknowns to be computed).

Next, the module 20 calls up and obtains the value of the material constant $C^U$ of Urethane U, the value of the material constant $C^P$ of Epoxy P and the value of the volume fraction $v_u$ of Urethane U from the database stored in the storage device 30 (Step S10). In this case, the material constants $C^U$ and $C^P$ are represented in terms of the Lamé constants, $\lambda$ and $\mu$. The values of the material constants and the volume fraction are fed into the nonlinear equation setting module 22, and the values of the coefficients in Equation (5) are therein set. Thus, Equation (5) is modified to be interpreted as a recursive nonlinear equation having the material constant $C^*$ as the only unknown. In other words, an equation is herein prepared.

Next, the equation solver module 24 sets initial values of the Lamé constants $\lambda_{ef}$ and $\mu_{ef}$ that is, the unknown components of the material constant $C^*$ (Step S20). The initial values are set because Equation (5) is a nonlinear equation and computation is repeatedly executed until convergence is reached. Any suitable value may be given as initial values. However, a good choice would be, for instance, the volume average using the material constant $C^P$ of Epoxy P (i.e., the matrix phase) and the material constant $C^U$ of Urethane U. The initial values of the Lamé constants $\lambda_{ef}, \mu_{ef}$ are set to be $\lambda_l$, $\mu_l$, respectively (i.e., $\lambda_{ef}=\lambda_l, \lambda_{ef}=\mu_l$). Furthermore, the initial values are represented as $\lambda_n, \mu_n$ (n=1), respectively.

Next, the equation solver module 24 defines Equation (16) derived by modifying Equation (5). Specifically, the left-hand side of Equation (5) is moved to the right-hand side thereof, and the newly produced right-hand side is defined as "$F(C^*)$."

Equation (16):

$$F(C^*) = C^A + v_B \cdot (C^B - C^A) \cdot A(C^B, C^*) - C^* \quad (16)$$

Furthermore, the module 24 defines $C^{(n+1)}$ with $F(C^*)$ in accordance with the following Equation (17). In this case, Equation (17) for obtaining convergence satisfying "$F(C^*)$ =0" is an equation to which the Newton-Raphson method is applied. Additionally, $C^{(n)}$ is represented in terms of the Lamé constants $\lambda_n$, $\mu_n$ whereas $C^{(n+1)}$ is represented in terms of the Lamé constants $\lambda_{n+1}$, $\lambda_{n+1}$. The module 24 gives the Lamé constants $\lambda_n$, $\mu_n$ to $C^{(n)}$ in Equation (17), and accordingly computes and obtains the Lamé constants $\lambda_{n+1}$, $\mu_{n+1}$ in accordance with Equation (17) (Step S30). In this case, $F'(C^{(n)})$ in Equation (17) is the Jacobian tensor of $F(C^{(n)})$, and $F'(C^{(n)})^{-1}$ is the inverse tensor of $F'(C^{(n)})$. In other words, the following relation is satisfied: $F'(C^{(n)})^{-1} \cdot F'(C^{(n)}) = I$ ("I" is the identity tensor).

Equation (17):

$$C^{(n+1)} = C^{(n)} - F'(C^{(n)})^{-1} F(C^{(n)}) \quad (17)$$

The computed Lamé constants $\lambda_{n+1}$, $\mu_{n+1}$ and the Lamé constants $\lambda_n$, $\mu_n$ used for the computation of the Lamé constants $\lambda_{n+1}$, $\mu_{n+1}$ are fed into the convergence determination module 26. The module 26 computes the absolute value of the difference between $\lambda_{n+1}$ and $\lambda_n$ (i.e., the absolute value of "$\lambda_{n+1}-\lambda_n$") and the absolute value of the difference between $\mu_{n+1}$ and $\mu_n$ (i.e., the absolute value of "$\mu_{n+1}-\mu_n$"). The module 26 compares the absolute value of "$\lambda_{n+1}-\lambda_n$" with a preliminarily-set threshold of $\epsilon_1$, and also compares the absolute value of "$\mu_{n+1}-\mu_n$" with a preliminarily-set threshold of $\epsilon_2$ (Step S40). When the following condition is satisfied as a result of comparison: "the absolute value of "$\lambda_{n+1}-\lambda_n$" is less than the threshold $\epsilon_1$ and the absolute value of "$\mu_{n+1}-\mu_n$" is less than the threshold $\epsilon_2$," (Yes in Step S40), the Lamé constants $\lambda_{ef}$, $\mu_{ef}$ (i.e., the overall material constant $C^*_1$ of the first virtual composite material to be computed) are determined to be $\lambda_{n+1}$, $\mu_{n+1}$, respectively (Step S50). On the other hand, when the aforementioned condition is not satisfied as a result of comparison (No in Step S40), "n+1" is replaced by "n" (Step S60) and the computation processing returns to Step S30 for computing the Lamé constants $\lambda_{n+1}$, $\lambda_{n+1}$ with Equation (17). Thus, Steps S30, S40 and S60 are repeatedly executed until the condition of Step S40 is satisfied.

Next, the computed overall material constant $C^*_1$ of the first virtual composite material is used in Step S50, and the overall material constant $C^*_2$ of the second virtual composite material is computed in subsequent Steps S80 to S140. Specifically, the overall material constant $C^*_2$ is computed by defining the second virtual composite material to be the one that Filler F is dispersed in a homogeneous body having the material constant $C^*_1$ of the first virtual composite material.

The subsequent steps correspond to Steps S10 to S70, respectively. Therefore, a detailed explanation thereof will be hereinafter omitted.

First, the condition setting module 20 calls up and obtains the value of the material constant $C^F$ of Filler F, the value of the overall material constant $C^*_1$ of the first virtual composite material and the value of the volume fraction $v_F$ of Filler F from the database stored in the storage device 30 (Step S80).

Next, the equation solver module 24 sets initial values of the Lamé constants $\lambda_{ef}$ and $\mu_{ef}$ (i.e., unknowns of the material constant $C^*_2$) to be $\lambda_m$, $\lambda_m$ (m=1), respectively (Step S90).

Next, the module 24 gives the value of the m-th sequence of the material constant (i.e., the values of Lamé constants) to the material constant $C^*$ in the right-hand side of Equation (17). Accordingly, the module 24 computes the (m+1)-th sequence of the material constant (i.e., the Lamé constants) in the left-hand side of Equation (17) (Step S100).

Next, the Lamé constants $\lambda_{m+1}$, $\lambda_{m+1}$ computed in Step S100 and the Lamé constants $\lambda_m$ and $\mu_m$ used for computing the Lamé constants $\lambda_{m+1}$, $\lambda_{m+1}$ are fed into the convergence determination module 26. The module 26 compares the absolute value of the difference between "$\lambda_{m+1}$" and "$\lambda_m$" (i.e., the absolute value of "$\lambda_{m+1}-\lambda_m$") with a preliminarily-set threshold of $\epsilon_3$, and compares the absolute value of the difference between "$\mu_{m+1}$" and "$\mu_m$" (i.e., the absolute value of "$\mu_{m+1}-\mu_m$") with a preliminarily-set threshold of $\epsilon_4$" (Step S110). Specifically, the module 26 determines if the following condition is satisfied: "the absolute value of "$\lambda_{m+1}-\lambda_m$" is less than the preliminarily-set threshold $\epsilon_3$ and the absolute value of "$\mu_{m+1}-\mu_m$" is also less than the preliminarily-set threshold $\epsilon_4$." When the module 26 determines that the condition is satisfied as a result of comparison (Yes in Step S110), the Lamé constants $\lambda_{ef}$, $\mu_{ef}$ (i.e., the overall material constant $C^*_2$ of the second virtual composite material to be computed) are determined to be $\lambda_{m+1}$, $\mu_{m+1}$, respectively (Step S120). On the other hand, when the module 26 determines that the condition is not satisfied as a result of comparison (No in Step S110), "m+1" is replaced by "m" (Step S130), and the computation processing returns to Step S100 for computing the Lamé constants $\lambda_{m+1}$, $\mu_{m+1}$.

Thus, Steps S100, S110 and S130 will be repeatedly executed until the module 26 determines that the condition of Step S100 is satisfied.

The overall material constant $C^*_2$ of the second virtual composite material computed in Step S120 is determined as the overall material constant $C^*$ of the composite material which includes Filler F and Urethane U in Epoxy P.

Next, the Young modulus $E^*$ is computed using the overall material constant $C^*$ of the composite material thus determined, specifically, the Lamé constants $\lambda^*$, $\mu^*$. The Young modulus $E^*$ is computed using Equation (18). The computed Young modulus $E^*$ is outputted to the output device 34 (e.g., a printer and a display).

Equation (18):

$$E^* = \frac{\mu^*(3\lambda^* + 2\mu^*)}{\lambda^* + \mu^*} \quad (18)$$

The computed Young modulus $E^*$ is in good agreement with the Young modulus E computed using a finite element model as hereinafter described. Therefore, it is clear that the method of computing the material constant of the composite material employing the present invention is beneficial. Furthermore, the method of the present invention is capable of analytically computing the material constant of the composite material using Equation (5). Accordingly, the method of the present invention is capable of computing the material constant of the composite material in a shorter period of time than the method using a finite element model. In this regard, the method of the present invention is more efficient than the method using a finite element model.

Equation (5), used in the method of the present invention for computing the material constant of the composite material, is an analytic equation. For example, the volume fraction of a predetermined material component may be accordingly chosen to be an unknown to be computed. In this case, the overall material constant of the composite material is required to be preliminarily acquired by an experiment. Computation of the volume fraction of the predetermined material component corresponds to the aforementioned second processing. The following is a specific explanation of the second processing.

Figure 7:
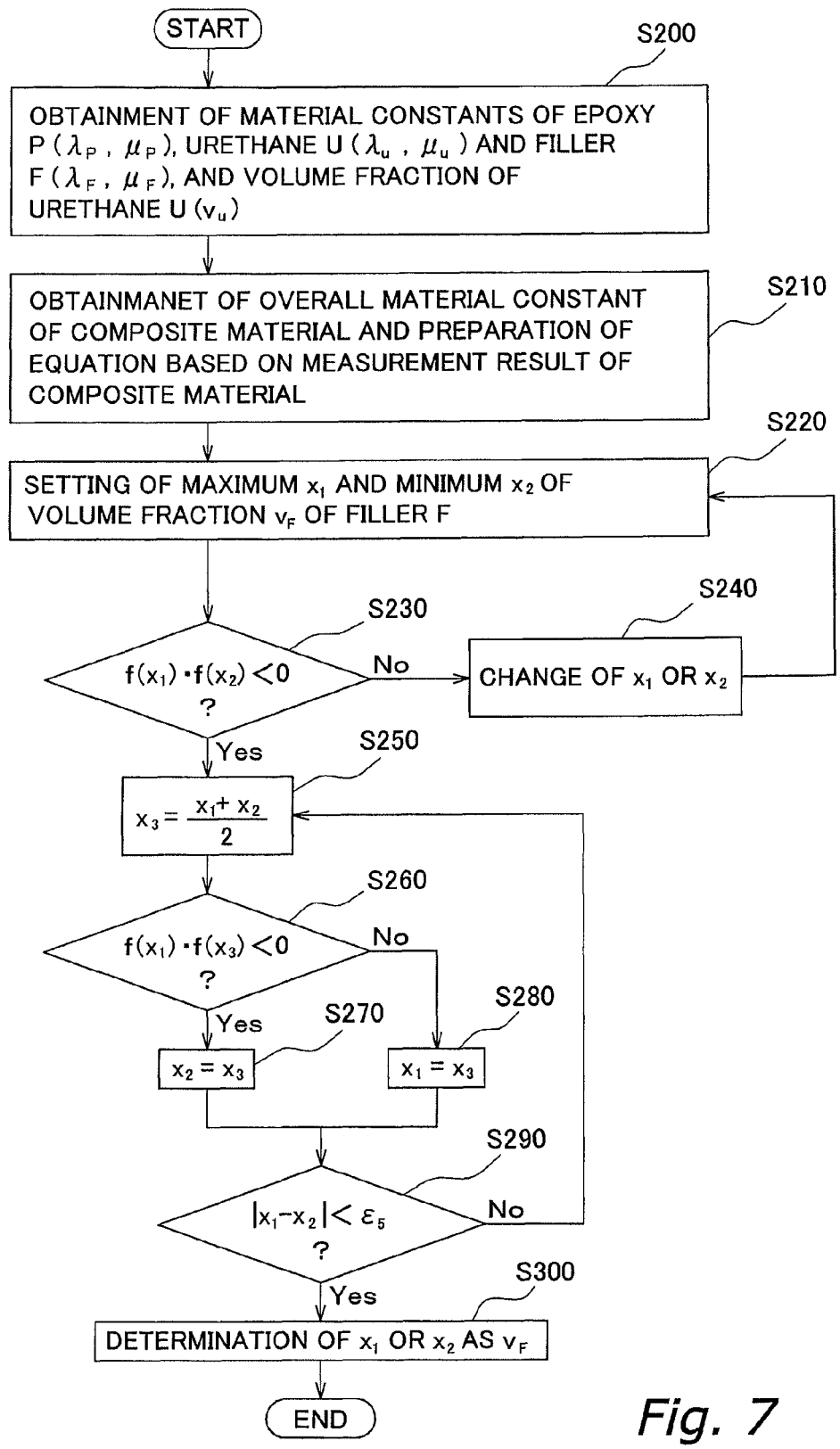
FIG. 7 is a flowchart for illustrating an example of the method of computing the volume fraction of a material component in a composite material according to the present invention.

FIG. 7 is a flowchart for illustrating a series of steps of the second processing. The second processing herein assumes computation of the volume fraction $v_F$ of Filler F in a composite material which includes Filler F and Urethane U in Epoxy P.

First, the condition setting module 20 obtains the material constant of Epoxy P (specifically $\lambda_P$, $\mu_P$), the material constant of Urethane U (specifically $\lambda_U$, $\mu_U$), the material constant of Filler F (specifically $\lambda_F$, $\mu_F$) and the volume fraction $v_U$ of Urethane U (Step S200). Specifically, the module 20 calls up and obtains the material constants and the volume fraction from the database stored in the storage device 30. Alternatively, the module 20 obtains the material constants and the volume fraction to be inputted through the input device 32.

Next, the overall material constants of the composite material (specifically $\lambda^*$, $\mu^*$) are obtained from a measurement result of a mechanical experiment of the composite material, and an equation is prepared (Step S210). The measurement result has been preliminarily stored in the storage device 30. The module 20 calls up the measurement result from the storage device 30 and obtains the material constant of the composite material. The nonlinear equation setting module 22 gives values of the material constants obtained in Steps S200 and S210 to the coefficients in Equation (5), and thus sets an equation having the volume fraction $v_F$ as an unknown. Furthermore, the function f(x) is defined using Equation (5) as follows: f(x)=(the overall material constant of the composite material acquired by an experiment)−(the overall material constant of the composite material with a volume fraction x to be computed in Equation (5)). In this case, the volume fraction x in the function f(x) is the volume fraction of Filler F, and Equation (5) to be used in the function f(x) is an equation for computing the overall material constant of the second virtual composite material in which Filler F is dispersed in the first virtual composite material (i.e., the matrix phase). The material constants of Urethane U and Epoxy P and the volume fraction of Urethane U are known. Therefore, it is possible to compute, by solving Equation (5), the overall material constant of the first virtual composite material which includes Urethane U in Epoxy P (i.e., the matrix phase). Accordingly, the overall material constant of the first virtual composite material is known.

Subsequently, the maximum $x_1$ and the minimum $x_2$ of the volume fraction $v_F$ are respectively set (Step S220). The maximum and the minimum of the volume fraction $v_F$ are set for computing the volume fraction $v_F$ using the bisection method as hereinafter described. The maximum and the minimum of the volume fraction $v_F$ may be set by an instruction inputted by an operator through the input device 32. Alternatively, preliminarily-set default values may be used as the maximum and the minimum of the volume fraction $v_F$.

Next, the equation solver module 24 uses the maximum $x_1$ and the minimum $x_2$ to compute $f(x_1) \cdot f(x_2)$ and the convergence determination module 26 determines if the sign of $f(x_1) \cdot f(x_2)$ is negative (Step S230). When the module 26 determines that the sign of $f(x_1) \cdot f(x_2)$ is positive, the maximum $x_1$ and the minimum $x_2$ are changed (Step S240). A method of changing the maximum and the minimum is not limited to a specific method. However, the maximum $x_1$ is desirably changed to be as large as possible whereas the minimum $x_2$ is desirably changed to be as small as possible because "$x_1$" and "$x_2$" are volume fractions.

When the module 26 determines that the sign of $f(x_1) \cdot f(x_2)$ is negative (Yes in Step S230), the following processing will be executed based on the bisectional method.

Specifically, the module 26 firstly computes "$x_3=(x_1+x_2)/2$" (Step S250), and the module 26 determines if the sign of $f(x_1) \cdot f(x_3)$ is negative (Step S260). When the module 26 determines that the sign of $f(x_1) \cdot f(x_3)$ is negative (Yes in Step S260), the minimum "$x_2$" is replaced by "$x_3$" (Step S270). On the other hand, when the module 26 determines that the sign of $f(x_1) \cdot f(x_3)$ is not negative (No in Step S260), the maximum "$x_1$" is replaced by "$x_3$" (Step S280).

Subsequently, the module 26 determines if the absolute value of the difference between the maximum $x_1$ and the minimum $x_2$ is less than a preliminarily-set threshold of $\epsilon_5$ (Step S290). When the module 26 determines that the absolute value is less than the threshold $\epsilon_5$ (Yes in Step S290), the maximum $x_1$ or the minimum $x_2$ is determined as the volume fraction $v_F$ to be computed (Step S300). When the module 26 determines that the absolute value is not less than the threshold $\epsilon_5$ (No in Step S290), the computation processing returns to Step S250. Thus, Steps S250, S260, S270 and S280 are repeatedly executed until the module 26 determines that the absolute value is less than the threshold $\epsilon_5$ in Step S290.

With the aforementioned method, the volume fraction $v_F$ of Filler F is computed. The computed volume fraction $v_F$ of Filler F is outputted to the output device 34.

Note that not only the volume fraction of Filler F but also the volume fraction of Urethane U may be chosen as an intended volume fraction to be computed. Additionally, volume fractions of multiple kinds of material components may be chosen as intended volume fractions to be computed.

As described above, the composite material which includes two different kinds of material components in the matrix phase is used for explaining the method of computing the effective material constant of the composite material and the method of computing the volume fraction according to the present invention. However, the composite material may include only a single kind of material component in the matrix phase. Alternatively, the composite material may include three kinds of material components in the matrix phase. Furthermore, the matrix phase may not be limited to epoxy. For example, any suitable inorganic material (e.g., metal or ceramic) may be used as the matrix phase. On the other hand, material components in the matrix phase, may not be limited to a reinforcement material for reinforcing the matrix phase. For example, any suitable soft material (e.g., urethane) may be used as the material component as described above.

Furthermore, a single or multiple kinds of material components, included in the matrix phase of the composite material, may not be necessarily dispersed in the form of particles. For example, the material component(s) may be resolved and mixed with the matrix phase. In the aforementioned case, the material constant of the composite material is computed by assuming that Urethane U is resolved and mixed with Epoxy P.

Furthermore, the method of computing the material constant of the composite material and the method of computing the volume fraction are also achieved by causing a computer to run a program. In this case, the program is recorded in a computer-readable recording medium. Additionally, the recoding medium includes a program downloaded through the communication network.

Next, validation of the method of computing the overall material constant of the composite material will be hereinafter explained. The following is a list of materials used for the composite material.

(1) Epoxy and Urethane of 60 g, including the following:
  Urethane modified epoxy of 30 g;
  NBR modified epoxy of 20 g; and
  Bisphenol A-type liquid epoxy of 10 g (2) Filler of 35 g, including the following:
   Silica of 15 g;
   Calcium carbonate of 10 g; and
   Calcium oxide of 10 g
(3) Curing material of 5 g, including the following:
   DICY (Dicyandiamide) of 5 g.

The following are the Young moduli, the Poisson ratios and the volume fractions (%) of the components of the composite material. In this case, the Young moduli and the Poisson ratios were converted into the Lamé constants using a known equation, and the obtained Lamé constants are herein used.

|          | Young's Modulus (GPa) | Poisson's Ratio | Volume Fraction (%) |
|----------|-----------------------|-----------------|---------------------|
| epoxy P  | 3.8                   | 0.35            | 54                  |
| urethane U | 0.1                 | 0.45            | 32                  |
| filler F | 35                    | 0.27            | 14                  |

The Young modulus was computed to be 1.819 (GPa) as a result of computing the overall material constant of the composite material according to the present invention. On the other hand, the Young modulus was computed to be 1.748 (GPa) as a result of an analysis of the composite material using the finite element model.

Consequently, the effective Young modulus computed using the method of the present invention is in good agreement with the effective Young modulus computed using the finite element model. Therefore, it is clear that the method of the present invention is beneficial.

Figure 8A:
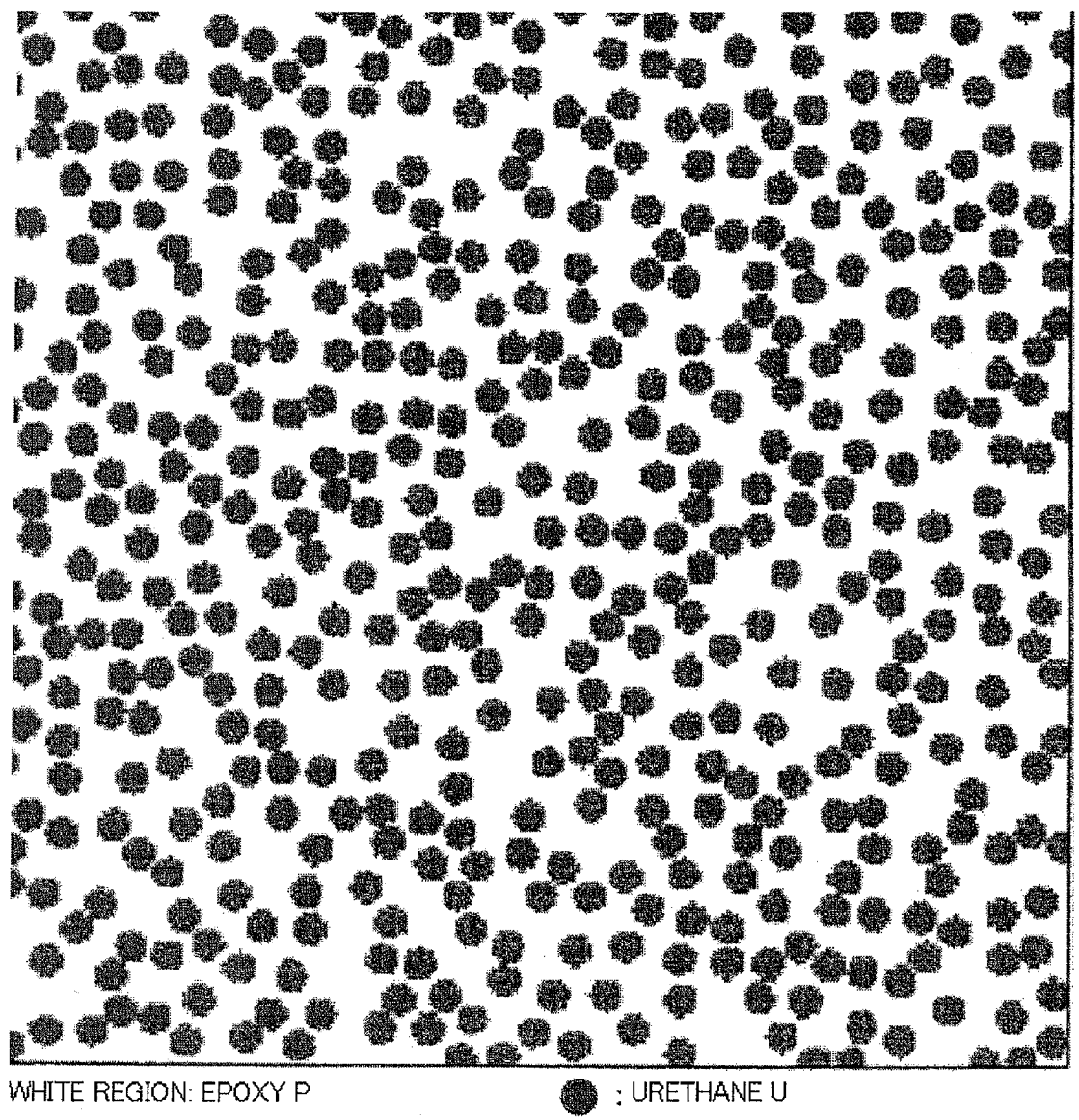
FIGS. 8A and 8B are diagrams for illustrating a finite element model of the composite material.
Figure 8B:
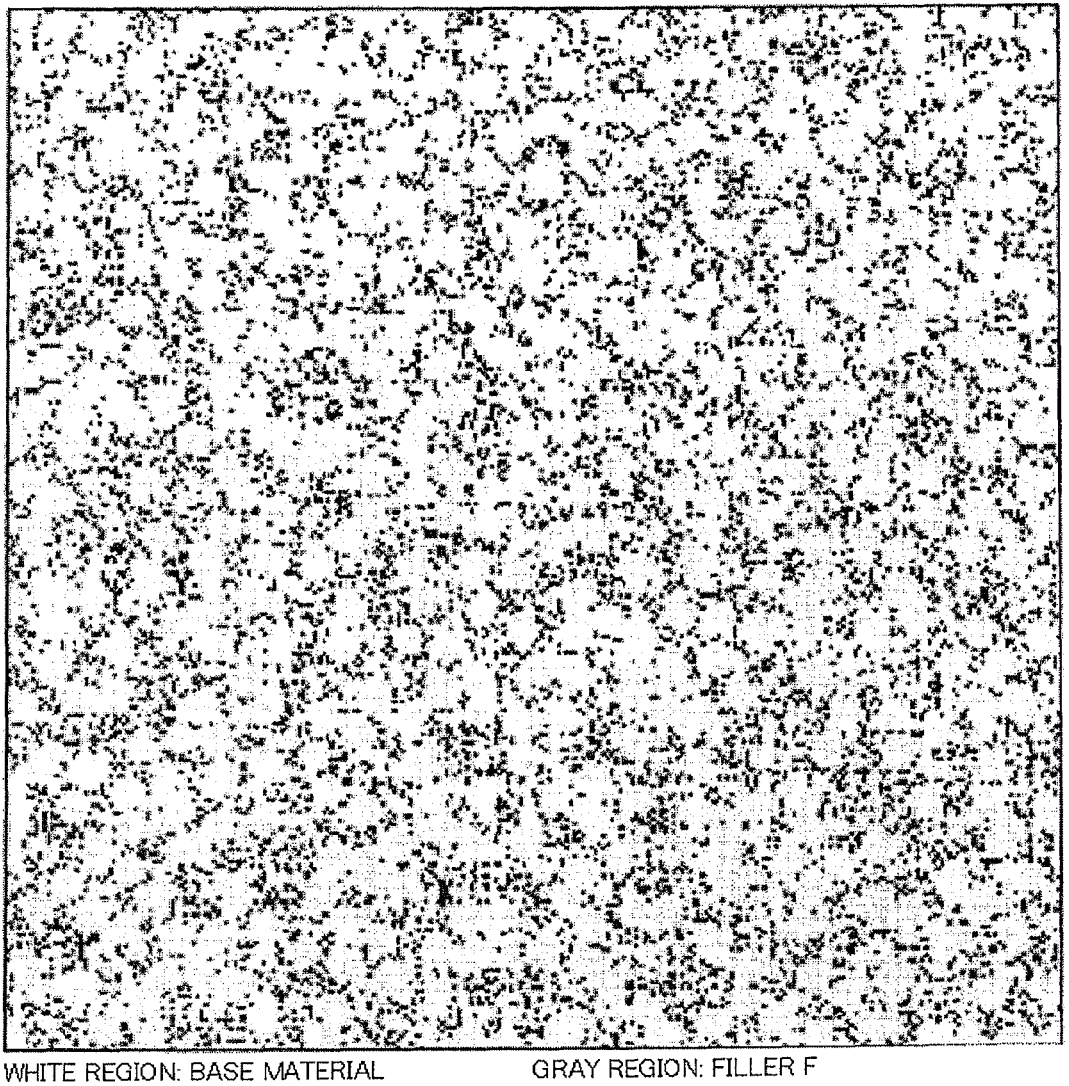

Note that computation of the material constant was executed using a finite element model as follows. First, a finite element model was produced by assuming the following base material. As illustrated in FIG. 8A, the base material was composed of Epoxy P (i.e., the matrix phase) and Urethane U of spherical shape. Urethane U was contained in Epoxy P at the volume fraction of 37.2%(=32/(32+54)×100). Based on this, the overall material constant of the base material was computed. Next, another finite element model was produced by assuming the following composite material. As illustrated in FIG. 8B, the composite material was composed of the assumed base material (i.e., the matrix phase) and Filler F. Filler F was contained in the base material at the volume fraction of 14%. Then, the overall material constant of the composite material was computed. Both in the cases above, the initial slope of stress-strain curve was computed under the condition that a tensile displacement was applied to the upper end shown in FIGS. 8A and 8B. Based on this, the Young modulus was obtained. Note that both of the above-produced finite element models were two-dimensional plane stress element models having 65536 elements and 66049 nodes. Furthermore, "ABAQUS," commercial software of a nonlinear finite element method, was used for the analysis.

As described above, the embodiment of the present invention specifically explains the method of computing the material constant of a composite material, the method of computing the volume fraction of a material component in a composite material, and a recording medium storing a program for causing a computer to execute the methods. However, the present invention is not limited to the aforementioned embodiment. Obviously, a variety of changes and modifications may be possible with respect to the present invention without departing from the scope of the present invention.

What is claimed is:

1. A method of computing an overall mechanical material constant of a composite material which includes a first material component in a matrix phase, each of mechanical material constants of the first material component and the matrix phase being known, the method comprising:
   controlling a nonlinear equation setting component of a computer to prepare a nonlinear equation having an overall material constant of a virtual composite material as an unknown by defining the virtual composite material in which the first material component is dispersed in a form of spherical particles in the matrix phase at a known volume fraction; and
   controlling an equation solver component of the computer to compute the overall material constant of the virtual composite material as an overall material constant of the composite material by solving the prepared nonlinear equation,
   wherein the nonlinear equation is a recursive nonlinear equation which is obtained by determining, as the overall material constant of the virtual composite material to be computed, a material constant in surrounding areas of the spherical particles in the virtual composite material.

2. The method according to claim 1,
   wherein the nonlinear equation is expressed as "$C^* = C^A + v_B \cdot (C^B - C^A) \cdot A(C^B, C^*)$" when the material constant of the matrix phase, the material constant of the first material component, the volume fraction of the first material component and the overall material constant of the virtual composite material are represented as $C^A$, $C^B$, $v_B$ and $C^*$, respectively, and
   wherein an expression "$A(C^B, C^*)$" in the equation is obtained by defining the material constant in the surrounding areas of the spherical particles in the virtual composite material as the overall material constant of the virtual composite material to be computed, and an expression "$A(C^B, C^*)$" is a proportional constant to be defined by a nonlinear equation having the material constant $C^*$ as an unknown.

3. The method according to claim 1, wherein,
   when each of stress and strain of the virtual composite material is decomposed into a shear term and a hydrostatic pressure term, and a displacement corresponding to the hydrostatic pressure term in the virtual composite material is defined as $u_i$ (i=1, 2 or 3),
   the nonlinear equation is prepared by defining,
      the displacement $u_i$ inside each of the spherical particles of the first material component to be proportional to a position $x_i$ (i=1, 2 or 3) with an origin at a center of each of the spherical particles; and
      the displacement $u_i$ outside each of the spherical particles to have:
   a term which is proportional to a position $x_i$ (i=1, 2 or 3) with the origin at the center of each of the spherical particles and a term which is proportional to the position $x_i$ and inversely proportional to third power of a distance from the center of each of the spherical particles.

4. The method according to claim 1, wherein,
   when each of stress and strain of the virtual composite material is decomposed into a shear term and a hydrostatic pressure term, and a displacement of the virtual composite material corresponding to the shear term is defined as $u_i$ (i=1, 2 or 3),
   the nonlinear equation is prepared by defining a displacement $u_i$ inside and outside each of the spherical particles using a combination of terms proportional to zeroth-power, second-power, inverse third-power and fifth power of a distance from a center of each of the spherical particles of the first material component.

5. The method according to claim 1, wherein the nonlinear equation is solved using the Newton-Raphson method for a solution to reach convergence.

6. A method of computing an overall mechanical material constant of composite material which includes a first material component and a second material component in a matrix phase, each of mechanical material constants of the first material component, the second material component and the matrix phase being known, the method comprising:
controlling a nonlinear equation setting component of a computer to prepare a first nonlinear equation having an overall material constant of a first virtual composite material as an unknown by defining the first virtual composite material in which the first material component is dispersed in a form of spherical particles in the matrix phase at a known volume fraction;
controlling an equation solver component of the computer to compute the overall material constant of the first virtual composite material by solving the prepared first nonlinear equation;
controlling the nonlinear equation setting component of the computer to prepare a second nonlinear equation having an overall material constant of a second virtual composite material as an unknown by defining the second virtual composite material in which the second material component is dispersed in a form of spherical particles in a virtual matrix phase having the computed overall material constant of the first virtual composite material at a known volume fraction; and
controlling the equation solver component of the computer to compute the overall material constant of the second virtual composite material as an overall material constant of the composite material by solving the prepared second nonlinear equation, and
wherein the first nonlinear equation is a recursive nonlinear equation which is obtained by defining a material constant in surrounding areas of the spherical particles as the overall material constant of the first virtual composite material to be computed, and
wherein the second nonlinear equation is also a recursive nonlinear equation which is obtained by defining the material constant in surrounding areas of the spherical particles as the material constant of the second virtual composite material to be computed.

7. The method according to claim 6, wherein,
when the material constants of the matrix phase and the virtual matrix phase, the material constants of the first material component and the second material component, the volume fractions of the first material component and the second material component, and the overall material constants of each of the first virtual composite material and the second virtual composite material are represented as $C^A$, $C^B$, $V_B$, and $C^*$, respectively, both of the first and second nonlinear equations are represented as "$C^*=C^A+v_B \cdot (C^B-C^A) \cdot A(C^B, C^*)$," and
wherein an expression "$A(C^B, C^*)$" in each of the equations is obtained by defining the material constant in the surrounding areas of the spherical particles in the virtual composite material as the overall material constant of the first virtual composite material or the second virtual composite material, and the expression "$A(C^B, C^*)$" is a proportional constant to be defined by a nonlinear formula having the material constant $C^*$ as an unknown.

8. The method according to claim 6, wherein,
when each of stress and strain of the first virtual composite material and the second virtual composite material is decomposed into a shear term and a hydrostatic pressure term, and each of displacements corresponding to the hydrostatic pressure term in the first virtual composite material and the second virtual composite material is defined as $u_i$ (i=1, 2 or 3),
each of the first and second nonlinear equations is prepared by defining,
the displacement $u_i$ inside each of the spherical particles of the first or second material component to be proportional to a position $x_i$ (i=1, 2 or 3) with an origin at the center of each of the spherical particles; and
the displacement $u_i$ outside each of the spherical particles to have:
a term which is proportional to a position $x_i$ (i=1, 2 or 3) with an origin at a center of each of the spherical particles and a term which is proportional to the position $x_i$ and inversely proportional to third power of a distance from the center of each of the spherical particles.

9. The method according to claim 6, wherein,
when each of stress and strain of the first virtual composite material and the second virtual composite material is decomposed into a shear term and a hydrostatic pressure term, and each of displacement corresponding to the shear term of the first virtual composite material and the second virtual composite material is defined as $u_i$ (i=1, 2 or 3), each of the nonlinear equations is prepared by defining the displacement $u_i$ as a combination of terms proportional to zeroth-power, second-power, inverse third-power and fifth-power of a distance from a center of each of the spherical particles of the first or second material component, both inside and outside each of the spherical particles.

10. The method according to claim 6, wherein each of the first and second nonlinear equations is solved using the Newton-Raphson method for a solution to reach convergence.

11. A method of computing a volume fraction of a first material component in a composite material which includes the first material component in a matrix phase, each of mechanical material constants of the first material component and the matrix phase being known, the method comprising:
controlling a condition setting component of a computer to determine an overall material constant of the composite material from an experimental result;
controlling a nonlinear equation setting component of the computer to prepare a nonlinear equation having a volume fraction of a first material component in a virtual composite material as an unknown by defining the virtual composite material in which the first material component is dispersed in a form of spherical particles in the matrix phase; and
controlling an equation solver component of the computer to compute the volume fraction of the first material component by solving the prepared nonlinear equation, and
wherein the nonlinear equation is a recursive nonlinear equation which is obtained by defining, as the determined overall material constant of the composite material, a material constant in surrounding areas of the spherical particles in the virtual composite material.

12. The method according to claim 11, wherein,
when the material constant of the matrix phase, the material constant of the first material component, the overall material constant of the composite material and the volume fraction of the first material, to be computed, are represented as $C^A$, $C^B$, $C^*$ and $v_B$, respectively, the nonlinear equation is represented as "$C^* = C^A + v_B \cdot (C^B - C^A) \cdot A(C^B, C^*)$," and wherein an expression "$A(C^B, C^*)$" in the equation is obtained by defining the material constant in the surrounding areas of the spherical particles in the virtual composite material as the overall material constant of the composite material, and the expression $A(C^B, C^*)$ is a proportional constant to be defined by a nonlinear formula having the material constant $C^*$ as an unknown.

13. The method according to claim 11, wherein,
when each of stress and strain of the virtual composite material is decomposed into a shear term and a hydrostatic pressure term and a displacement corresponding to the hydrostatic pressure term in the virtual composite material is defined as $u_i$ (i=1, 2 or 3),
the nonlinear equation is prepared by defining,
the displacement $u_i$ inside each of the spherical particles of the first material component to be proportional to a position $x_i$ (i=1, 2 or 3) with an origin at the center of each of the spherical particles; and
the displacement $u_i$ outside the spherical particle to have:
a term which is proportional to the position $x_i$ (i=1, 2 or 3) with the origin at the center of each of the spherical particles and a term which is proportional to the position $x_i$ and inversely proportional to third power of a distance from the center of each of the spherical particles.

14. The method according to claim 11, wherein,
when each of stress and strain of the virtual composite material is decomposed into a shear term and a hydrostatic pressure term and a displacement corresponding to the shear term in the virtual composite material is defined as $u_i$ (i=1, 2 or 3),
the nonlinear equation is prepared by defining the displacement $u_i$ as a combination of terms proportional to zeroth-power, second-power, inverse third-power and fifth power of distance from a center of each of the spherical particles of the first material component, respectively, both inside and outside each of the spherical particles.

15. The method according to claim 11, wherein the nonlinear equation is solved using the bisectional method.

16. A method of computing a volume fraction of a second material component in a composite material which includes a first material component and the second material component in the matrix phase, each of the mechanical material constants of the first material component, the second material component and the matrix phase being known, the method comprising:
controlling a condition setting component of a computer to determine the overall material constant of the composite material from an experimental result;
controlling a nonlinear equation setting component of the computer to prepare a third nonlinear equation having the volume fraction of the second material as an unknown by defining a first virtual composite material in which the first material component is dispersed in a form of spherical particles in the matrix phase at a known volume fraction and by further defining a second virtual composite material in which the second material component is dispersed in a form of spherical particles in a virtual matrix phase having an overall material constant of the first virtual composite material at a unknown volume fraction; and
controlling an equation solver component of the computer to compute the volume fraction of the second material by solving the prepared third nonlinear equation, and wherein the third nonlinear equation is a recursive nonlinear equation which is obtained by defining, as the overall material constant of the first virtual composite material, a material constant in surrounding areas of the spherical particles in the first virtual composite material and by defining, as the determined overall material constant of the composite material, a material constant in the surrounding areas of the spherical particles in the second virtual composite material.

17. The method according to claim 16, wherein,
when the material constants of the matrix phase and the virtual matrix phase, the material constants of either the first material component or the second material component, the volume fraction of either one of the first material component or the second material component, and the material constants of either one of the first virtual composite material or the second virtual composite material are represented as $C^A$, $C^B$, $v_B$ and $C^*$, respectively,
the third nonlinear equation is formed by a combination of a first equation for computing the overall material constant of the first virtual composite material and a second equation for computing the overall material constant of the second virtual composite material, and both the first and second nonlinear equations are represented as "$C^* = C^A + v_B \cdot (C^B - C^A) \cdot A(C^B, C^*)$," and
wherein an expression "$A(C^B, C^*)$" in the equation is obtained by defining the material constant in the surrounding areas of the spherical particles in the first virtual composite material as the overall material constant of the first virtual composite material and by defining the material constant in the surrounding area of the spherical particles in the second virtual composite material as the determined overall material constant of the composite material, and an expression "$A(C^B, C^*)$" is a proportional constant to be defined by a nonlinear formula having the material constant $C^*$ as an unknown.

18. The method according to claim 16, wherein,
when each of stress and strain of the first virtual composite material and the second virtual composite material is decomposed into a shear term and a hydrostatic pressure term, and each of displacements corresponding to the hydrostatic pressure term in the first virtual composite material and the second virtual composite material is defined as $u_i$ (i=1, 2 or 3),
the nonlinear equation is prepared by defining,
the displacement $u_i$ inside each of the spherical particles of the first material component and the second material component to be proportional to a position $x_i$ (i=1, 2 or 3) with an origin at a center of the spherical particle; and
the displacement $u_i$ outside the spherical particle to have:
a term which is proportional to a position $x_i$ (i=1, 2 or 3) with the origin at the center of the spherical particle and a term which is proportional to the position $x_i$ and inversely proportional to third power of a distance from the center of the spherical particle.

19. The method according to claim 16, wherein,
when each of stress and strain of the first virtual composite material and the second virtual composite material is decomposed into a shear term and a hydrostatic pressure term, and each of displacements corresponding to the shear term in the first virtual composite material and the second virtual composite material is defined as $u_i$ (i=1, 2 or 3), the nonlinear equation is prepared by defining the displacement $u_r$ as a combination of terms proportional to zeroth-power, second-power, inverse third-power and fifth-power of distance from a center of each of the spherical particles, respectively, both inside and outside each of the spherical particles.

20. The method according to claim 16, wherein the nonlinear equation is solved using the bisectional method.

21. A non-transitory computer-readable medium storing a computer-executable program for computing an overall mechanical material constant of a composite material which includes a first material component in a matrix phase, each of mechanical material constants of the first material component and the matrix phase being known, wherein the program causes a computer to execute the operations of:
preparing a nonlinear equation having an overall material constant of a virtual composite material as an unknown by defining the virtual composite material in which the first material component is dispersed in a form of spherical particles in the matrix phase at a known volume fraction and;
computing the overall material constant of the virtual composite material as the material constant of the composite material by solving the prepared nonlinear equation, and
wherein the nonlinear equation is a recursive nonlinear equation which is obtained by defining, as the overall material constant of the virtual composite material to be computed, a material constant in surrounding areas of the spherical particles in the virtual composite material.

22. A non-transitory computer-readable medium storing a computer-executable program for computing an overall mechanical material constant of a composite material which includes a first material component and a second material component in a matrix phase, each of mechanical material constants of the first material component, the second material component and the matrix phase being known, wherein the program causes a computer to execute the operations of:
preparing a first nonlinear equation having an overall material constant of a first virtual composite material as an unknown by defining the first virtual composite material in which the first material component is dispersed in a form of spherical particles in the matrix phase at a known volume fraction;
computing the overall material constant of the first virtual composite material by solving the prepared first nonlinear equation;
preparing a second nonlinear equation having an overall material constant of a second virtual composite material as an unknown by defining the second virtual composite material in which a second material component is dispersed in a form of spherical particles in a virtual matrix phase having the computed effective material constant of the first virtual composite material at a known volume fraction; and
computing the overall material constant of the second virtual composite material as the overall material constant of the composite material by solving the prepared second nonlinear equation, and
wherein each of the first and second nonlinear equations is a recursive nonlinear equation which is obtained by defining, as the overall material constant of the first virtual composite material to be computed, a material constant in surrounding areas of the spherical particles in the first virtual composite material and by defining, as the overall material constant of the second virtual composite material to be computed, a material constant in surrounding areas of the spherical particles in the second virtual composite material.

23. A non-transitory computer-readable medium storing a computer-executable program for computing a volume fraction of a first material component in a composite material which includes the first material component in a matrix phase, each of mechanical material constants of the first material component and the matrix phase being known, wherein the program causes a computer to execute the operations of:
determining the overall material constant of the composite material from an experimental result;
preparing a third nonlinear equation having the volume fraction of the first material component as an unknown by defining a virtual composite material in which the first material component is dispersed in a form of spherical particles in the matrix phase at a known volume fraction; and
computing the volume fraction of the first material component by solving the prepared third nonlinear equation, and
wherein the third nonlinear equation is a recursive nonlinear equation which is obtained by defining, as the determined overall material constant of the composite material, a material constant in surrounding areas of the spherical particles in the virtual composite material.

24. A non-transitory computer-readable medium storing a computer-executable program for computing a volume fraction of a second material component in a composite material which includes a first material component and the second material component in a matrix phase, each of mechanical material constants of the first material constant, the second material constant and the matrix component being known, wherein the program causes a computer to execute the operations of:
determining the overall material constant of the composite material from an experimental result;
preparing a third nonlinear equation having the volume fraction of a second material component as an unknown by defining a first virtual composite material in which the first material component is dispersed in a form of spherical particles in the matrix phase at a known volume fraction and by further defining a second virtual composite material in which the second material component is dispersed in a form of spherical particles in a virtual matrix phase having the overall material constant of the first virtual composite material at an unknown volume fraction ; and
computing the volume fraction of the second material by solving the prepared third nonlinear equation, and
wherein the third nonlinear equation is a recursive nonlinear equation which is obtained by defining, as the overall material constant of the first virtual composite material, a material constant in surrounding areas of the spherical particles in the first virtual composite material and by defining, as the determined overall material constant of the composite material, a material constant in surrounding areas of the spherical particles in the second virtual composite material.

* * * * *